(12) United States Patent
Liu

(10) Patent No.: US 9,060,973 B2
(45) Date of Patent: *Jun. 23, 2015

(54) VACCINE FOR ENVELOPED VIRUSES

(76) Inventor: George Dacai Liu, Collegeville, PA (US)

(*) Notice: Subject to any disclaimer, the term of this patent is extended or adjusted under 35 U.S.C. 154(b) by 92 days.

This patent is subject to a terminal disclaimer.

(21) Appl. No.: 13/459,184

(22) Filed: Apr. 29, 2012

(65) Prior Publication Data

US 2013/0101612 A1   Apr. 25, 2013

Related U.S. Application Data

(63) Continuation-in-part of application No. 13/279,253, filed on Oct. 22, 2011, which is a continuation-in-part of application No. 13/279,250, filed on Oct. 22, 2011.

(51) Int. Cl.
| | | |
|---|---|---|
| *A61K 39/145* | (2006.01) | |
| *C07K 14/11* | (2006.01) | |
| *A61K 35/76* | (2015.01) | |
| *A61K 38/02* | (2006.01) | |
| *A61K 39/12* | (2006.01) | |
| *C07K 14/005* | (2006.01) | |
| *C07K 19/00* | (2006.01) | |
| *C07K 2/00* | (2006.01) | |
| *A61K 39/00* | (2006.01) | |

(52) U.S. Cl.
CPC ............... *A61K 39/145* (2013.01); *A61K 35/76* (2013.01); *C07K 19/00* (2013.01); *C07K 2/00* (2013.01); *A61K 38/02* (2013.01); *A61K 2039/5252* (2013.01); *A61K 2039/55566* (2013.01); *C07K 2319/00* (2013.01); *C07K 2319/03* (2013.01); *C07K 2319/72* (2013.01); *C12N 2760/16134* (2013.01); *A61K 39/12* (2013.01); *A61K 2039/5258* (2013.01); *C12N 2740/16034* (2013.01); *C07K 14/005* (2013.01); *C12N 2740/16122* (2013.01); *C12N 2760/16122* (2013.01)

(58) Field of Classification Search
None
See application file for complete search history.

(56) References Cited

U.S. PATENT DOCUMENTS

2002/0168392 A1* 11/2002 Manners et al. .............. 424/405
2005/0106177 A1* 5/2005 Sodroski et al. ........... 424/208.1

OTHER PUBLICATIONS

Nilsson et al., J. Mol. Biol., 1998, 284:1165-1175.*
Iqbalsyah et al., Protein Science, 2006, 15:1945-1950.*

* cited by examiner

*Primary Examiner* — Nicole Kinsey White
(74) *Attorney, Agent, or Firm* — George Dacai Liu

(57) ABSTRACT

The present invention provides a recombinant viral surface antigenic protein with enhanced stability. The present invention also provides a vaccine composition against enveloped viruses.

**8 Cla

VACCINE FOR ENVELOPED VIRUSES

CROSS REFERENCE TO RELATED APPLICATIONS

The present application is a continuation in part of applications of U.S. application Ser. No. 13/279,253, filed on Oct. 22, 2011, entitled of "RECOMBINANT HEMAGGLUTININ PROTEIN OF INFLUENZA VIRUS AND VACCINE CONTAINING THE SAME", and U.S. application Ser. No. 13/279,250, filed on Oct. 22, 2011, entitled of "RECOMBINANT ENVELOPE PROTEIN OF HLTMAN IMMUNODEFICIENCY VIRUS (HIV) AND VACCINE CONTAINING THE SAME"; the disclosure of which are herein incorporated in its entirety.

FIELD OF THE INVENTION

The present invention relates to vaccines for enveloped viruses.

BACKGROUND OF THE INVENTION

Many viruses (e.g., influenza viruses, human immunodeficiency virus (HIV), and infectious bronchitis virus (IBV)) have viral envelopes covering their internal proteins and genomes. The enveloped viruses belong to many families including herpesviruses, poxviruses, hepadnaviruses, flavivirus, togavirus, coronavirus, hepatitis D, orthomyxovirus, rhabdovirus, bunyavirus, filovirus, retroviruses, and hepadnavirus, which infect both human and animals. The envelopes typically are derived from portions of the host cell membranes, where major viral glycoproteins are present on the surfaces of the envelopes to form the viral surface antigens. The viral surface antigens are typically bundled to form spikes for mediating virus entry. The spikes usually contain homotrimers of surface antigens.

Influenza A viruses belong to the Orthomyxovirus family, and have a wide host range, including humans, horses, dogs, birds, and pigs. It is an enveloped, negative-sense RNA virus composed of a set of 8 RNA segments (abbreviated as PB2, PB1, PA, HA, NP, NA, M and NS) encoding at least 10 viral proteins. The HA segment encodes the hemagglutinin (HA) protein, where the HA protein forms a homotrimer, forming the spikes on the influenza viruses.

HIV is a retrovirus. For HIV-1, there are already 33 million infected individuals who each harbor a substantial array of HIV-1 quasi-species, which results in an enormous number of variants that are simultaneously seeded and circulating in the human population. HIV contains the trimeric Env glycoprotein (gp160) on its virion surfaces.

IBV is a coronavirus, causing severe damages in poultry, contains a trimeric S protein on its surface.

SUMMARY OF THE INVENTION

One aspect of the present invention provides a recombinant viral surface antigenic protein, wherein the viral surface antigenic protein in its native state forms a homotrimer on the surface of an enveloped virus. In one embodiment, the recombinant viral surface antigenic protein comprises a trimeric bundle of alpha-helix structures, wherein the trimeric bundle is formed by three mocules of the recombinant viral surface antigenic protein, and wherein each of the alpha-helix structures in the trimeric bundle contains at least one two-cysteine mini-domain selected from CxxC (SEQ ID NO 3), CxxxC (SEQ ID NO 4) or CxxxxC (SEQ ID NO 5), where x represents any amino acids; wherein when only one of the at least one two-cysteine minidomain (SEQ ID NO 4) is present, native influenza A virus H3 HA is excluded; whereby when the recombinant viral surface antigenic protein forms the homotrimer, the two cysteines in the two-cysteine minidomain could form a tandem disulfide bond belt, covalently tighting the homotrimer.

In another embodiment of the recombinant viral surface antigenic protein, the enveloped virus is one selected from the group consisting of herpesviruses, poxviruses, hepadnaviruses, flavivirus, togavirus, coronavirus, hepatitis D, orthomyxovirus, rhabdovirus, bunyavirus, filovirus, retroviruses, and hepadnavirus.

In another embodiment of the recombinant viral surface antigenic protein, the recombinant viral surface antigenic protein is encoded by a DNA sequence, and the DNA sequence is cloned into an in vivo expression vector; so that the recombinant HA expression vector is used as a DNA vaccine against the enveloped virus from which the viral surface antigenic protein is derived.

In another embodiment of the recombinant viral surface antigenic protein, the recombinant viral surface antigenic protein is present in a virus-like particle, virosome, or a recombinant enveloped virus.

Another aspect of the present invention provides a vaccine composition against an enveloped virus. In one embodiment, the vaccine composition comprises a recombinant viral surface antigenic protein, wherein the viral surface antigenic protein in its native state forms a homotrimer on the surface of the enveloped virus; wherein the recombinant viral surface antigenic protein comprises a trimeric bundle of alpha-helix structures, wherein the trimeric bundle is formed by three mocules of the recombinant viral surface antigenic protein, and wherein each of the alpha-helix structures in the trimeric bundle contains at least one two-cysteine mini-domain selected from CxxC (SEQ ID NO 3), CxxxC (SEQ ID NO 4) or CxxxxC (SEQ ID NO 5), where x represents any amino acids; wherein when only one of the at least one two-cysteine minidomain (SEQ ID NO 4) is present, native influenza A virus H3 HA is excluded; whereby when the recombinant viral surface antigenic protein forms the homotrimer, the two cysteines in the two-cysteine minidomain could form a tandem disulfide bond belt, covalently tighting the homotrimer; and a pharmaceutically acceptable ingredient.

In another embodiment of the vaccine composition, the enveloped virus is one selected from the group consisting of herpesviruses, poxviruses, hepadnaviruses, flavivirus, togavirus, coronavirus, hepatitis D, orthomyxovirus, rhabdovirus, bunyavirus, filovirus, retroviruses, and hepadnavirus.

In another embodiment of the vaccine composition, the recombinant viral surface antigenic protein is encoded by a DNA sequence, and the DNA sequence is cloned into an in vivo expression vector; so that the recombinant HA expression vector is used as a DNA vaccine against the enveloped virus from which the viral surface antigenic protein is derived.

In another embodiment, the vaccine composition, the recombinant viral surface antigenic protein is present in a virus-like particle, virosome, or a recombinant enveloped virus.

The objectives and advantages of the invention will become apparent from the following detailed description of preferred embodiments thereof in connection with the accompanying drawings.

DETAILED DESCRIPTION OF THE INVENTION

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, *Molecular Cloning: A Laboratory Mannual*, third edition (Sambrook and Russel, 2001); *Animal Cell Culture* (R. I. Freshmey, ed., 1987); *Current Protocols in Molecular Biology* (F. M. Ausubel et al., eds., 1987, including supplements through 2001); *Current Protocols in Immunology* (J. E. Coligan et al., eds., 1991); *The Immunoassay Handbook* (D. Wild, ed., Stockton Press NY, 1994); *Methods of Immunological Analysis* (R. Masseyeff, W. H. Albert, and N. A. Staines, eds., Weinheim:VCH Verlags gesellschaft mbH, 1993).

The enveloped viruses include herpesviruses, poxviruses, hepadnaviruses, flavivirus, togavirus, coronavirus, hepatitis D, orthomyxovirus, rhabdovirus, bunyavirus, filovirus, retroviruses, and hepadnavirus. Typically, an enveloped virus contains the surface antigens that are usually in the form of homotrimers. The monomer in each homotrimer contains an ectodoman, a transmembrane domain and a cytoplasmic domain. The ectodoman in some of the viral monomers (e.g., HA of influenza virus, gp160 of HIV) comprises extensive alpha-helixes that form a compact bundle to matain the trimeric structure. However, the ectodoman in some of the viral monomers (S protein of IBV) does not have much alpha-helix structure; thus the homotrimeric structure is maintained by their TM doman. The TM domain is usually in the form of alpha-helix structure, and bundled together.

In our daily lives, a bundle of parallel materials such as bamboos and hays is held tightly by belts. Now the question is whether any belt could be introduced into the bundle of alpha-helix structures of viral homotrimers if such bundle is present.

The present invention recalled that the disulfide bond (S—S) formed by two cysteines can be formed between two peptides; for example, IgG is a homodimer bounded by multiple inter-peptide disulfide bonds. In order to form a circular belt, the present invention explored whether it was feasible to introduce a pair of cysteines into each monomer so that a tandem of three disulfide bonds could be formed between the three monomers. As known, each turn in a helix contains 3.6 amino acids, where the pitch (advance per turn) is 0.54 nm, and the rise (advance per amino acid residue) is 0.15 nm. For a disulfide bond formed by two cysteines, the distance between their centers is 0.849 nm (two c-c bonds (0.154 nm per bond), two c-s bonds (0.17 nm per bond), and one s-s bond (0.201 nm)). The distance of 0.849 nm is about 1.57 pitch or 5.66 amino acids; it means that if two cysteines are not separated by more than 4 amino acids, a disulfide bond could be formed between two helices.

The present invention discovered that introduction of at least one pair of cysteines into the TMD of HA could stabilize the HA homotrimer (increased resistance to pH and temperature treatments) and enhance the cross reactive immune responses; the introduction was made on the assumption that the pair of cysteines could form a disulfide bond belt around the trimeric HA structure, gripping the HA trimers more tightly.

The present invention provides that the introduction of at least one pair of cysteines forming one of the three two-cysteine mini-domains ((CxxC (SEQ ID NO 1); CxxxC (SEQ ID NO 2); CxxxxC (SEQ ID NO 3)) into the bundled alpha-helix structures enables the formation of a tandem disulfide bond belt between the three monomers, where the 'x' in the mini-domains is any amino acids as long as they do not break the helix structure, preferably A, L, M, F, E, Q, H, K and R in an artificially created mini-domain. Illustratively, the three disulfide bonds between three monomers (monomer 1 with 1C1 and 1C2; monomer 2 with 2C1 and 2C2; monomer 3 with 3C1 and 3C2) are 1C1-2C2, 2C1-3C2, and 3C1-1C2. This tandem disulfide bond belt tightly grips the three monomers together to form a highly stabilized trimer. This discovery is of great significance because any trimeric protein represented by HAs could be manipulated to include at least one two-cysteine mini-domain so that the trimeric structure is stabilized by a covalent bond belt. When such HAs are used as antigens for vaccines in the forms of recombinant proteins, VLP or viruses, the vaccines would elicit enhanced intra-subtype or inter-subtype immune responses. It is surprising to note that the search for the presence of any two-cysteine mini-domains in the NCBI' protein database uncovered only one two-cysteine mini-domain falling into CxxxC (SEQ ID NO 4) that is present in the TMD of H3HA. Thus, the native H3HA proteins are explicitly excluded when a claim is made to the minidomain (SEQ ID NO 2) present in the TM domain of a viral surface antigen. It is to be noted that the situations in which one cysteine is present in the alpha-helix structure require one additional cysteine to be introduced, resulting in a sequence falling into one of the minidomains.

The introduction of a tandem disulfide bond belt into a recombinant viral surface antigen can be achieved using any suitable molecular biological methods, for example point mutation, insertion or replacement; they are well established and known in the art. The exemplary embodiments of producing the recombinant viral surface antigen include: (1) mutating two amino acid resides into cysteines in any alpha-helix structure that forms an alpha-helix bundle (e.g., TM domain) in a homotrimer to form a two-cysteine mini-domain with a sequence selected from CxxC (SEQ ID NO 1), CxxxC (SEQ ID NO 2), or CxxxxC (SEQ ID NO 3); (2) inserting a two-cysteine mini-domain into any alpha-helix structure that forms an alpha-helix bundle in a homotrimer as long as the insertion does not break the helix structure; (3) replacing a corresponding stretch of amino acids in any alpha-helix structure that forms an alpha-helix bundle in a homotrimer with one synthetic polypeptide containing a two-cysteine mini-domain; (4) replacing a corresponding stretch of amino acids in any alpha-helix structure that forms an alpha-helix bundle in a homotrimer with the one from one natural molecule containing a two-cysteine mini-domain for example H3TMD; (5) fusing the ectodomain of a viral surface antigen to the transmembrane domain and cytoplasmic tail of another protein, where the fused transmembrane contains at least one two-cysteine mini-domain.

The recombinant viral surface antigen in its trimeric form can be produced as a soluble protein, a membrane protein, a surface protein present in a virus-like particle or a surface protein present in a recombinant virus (e.g., produced by reverse genetics).

The primary goal of the present invention is to provide vaccines against enveloped viruses with enhanced stabilization of the viral trimeric antigens with the formation of at least one two-cysteine minidomain. One advantage of the introduction of the minidomains is to elicit inter-subtypic and/or intra-subtypic cross reactive immune responses.

It is to be noted that many biotech applications are lengthy for stuffing extensive materials including methods and procedures that are well established and known in the art because the biotechnology was viewed with low predictability so that the examiners might raise the rejections failing to provide adequate details for one skilled in the art to practice the invention (lack of enablement). As a biotech researcher, the inventor of the present invention firmly believes that the biotechnology as a whole has advanced enough in the past thirty years that many basic procedures are well established and known, and more importantly the results are as predictable as that in the arts of mechanic and electronic engineering. For example, with a known virus and sequences, the DNA fragments of the virus shall be certainly obtained by PCR amplification; with a DNA fragment with known sequence, it shall be predictably subcloned into any vector including expression vectors in vitro and in vivo; with a cloned expression vector, the cloned gene shall be predictably expressed and purified; a virus-like particle can also be generated with known techniques; and a recombinant influenza virus can be rescued from plasmid systems such as reverse genetics. As a patent attorney, I strongly believe that biotech patent applications have come to the age when no more unnecessary materials are stuffed into an application, just as an electronic patent application never includes the description of the function of a capacitor or an amplifier. The elimination of the stuffed unnecessary materials helps to avoid the waste of time for both examiners and clients, and also makes the principles of the invention to be easily understood. In view of this, the known methods and materials are not included in this application.

As used herein, a "vaccine" is an antigenic preparation that is used to induce an immune response in individuals. A vaccine can have more than one constituent that is antigenic.

As used herein, "non-protein carriers" are carriers which are not proteins and can be used to achieve multimeric display of influenza matrix and/or nucleoprotein.

The term "microcarrier" refers to a particulate composition which is insoluble in water and which has a size of less than about 150, 120 or 100 um, more commonly less than about 50-60 um, and may be less than about 10 um or even less than about 5 um. Microcarriers include "nanocarriers," which are microcarriers have a size of less than about 1 um, preferably less than about 500 nm. Microcarriers include solid phase particles such particles formed from biocompatible naturally occurring polymers, synthetic polymers or synthetic copolymers, although microcarriers formed from agarose or cross-linkded agarose may be included or excluded from the definition of microcarriers herein as well as other biodigradable materials known in the art. Solid phase microcarriers are formed from polymers or other materials which are non-erodible and/or non-degradable under mammlian physiological conditions, such as polystyrene, polypropylene, silica, ceramic, polyacrylamide, gold, latex, hydroxyapatite, and ferromagnetic and paramagnetic materials. Biodegradable solid phase microcarriers may be formed from polymers which are degradable (e.g., poly(lactic acid), poly(glycolic acid) and copolymers thereof, such as poly(D, L-lactide-co-glycolide) or erodible (e.g., poly(ortho esters such as 3,9-diethylidene-2,4,8,10-tetraoxaspiro[5,5]undecane (DETOSU) or poly(anhydrides), such as poly(anhydrides) of sebacic acid) under mammalian physiologicaly conditions. Microcarriers are typically spherical in shape, but microcarriers which deviate from spherical shape are also acceptable (e.g., ellipsoidal, rod-shaped, etc.). Due to their insoluble nature, some solid phase microcarriers are filterable from water and water-based (aqueous) solutions (e.g., using a 0.2 micron filter). Microcarriers may also be liquid phase (e.g., oil or lipid based), such as liposomes, iscoms (immune-stimulating complexes, which are stable complexes of cholesterol, phospholipid and adjuvant-active saponin) without antigen, or droplets or micelles found in oil-in-water or water-in-oil emulsions, such as MF59. Biodegradable liquid phase microcarriers typically incorporate a biodegradable oil, a number of which are known in the art, including squalene and vegetable oils. The term "nonbiodegradable", as used herein, refers to a microcarrier which is not degraded or eroded under normal mammalian physiological conditions. Generally, a microcarrier is considered nonbiodegradable if it no degraded (i.e., loses less than 5% of its mass or average polymer length) after a 72 hour incubation at 37 oC in normal human serum.

An "individual" or "subject" is a vertebrate including avian (such as chickens, ducks and geese), and a mammal. Mammals include, but are not limited to, humans, non-human primates, farm animals, sport animals, experimental animals, rodents (e.g., mice and rats) and pets.

An "effective amount" or a "sufficient amount" of a substance is that amount sufficient to effect a desired biological effect, such as beneficial results, including clinical results, and as such, an "effective amount" depends upon the context in which it is being applied. In the context of this invention, an example of an effective amount of a composition comprising the desired antigen is an amount sufficient to induce an immune response in an individual. An effective amount can be administered in one or more administrations.

"Stimulation" of an immune response, such as humoral or cellular immune response, means an increase in the response, which can arise from eliciting and/or enhancement of a response.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of infection, stabilized (i.e., not worsening) state of infection, amelioration or palliation of the infectious state, and remission (whether partial or total), whether detectable or undetectable. "Treatment" can also mean prolonging survival as compared to expected survival if not receiving treatment.

According to the present invention, a "dose" of a vaccine composition, is a quantity of vaccine composition that is administered at a particular point in time. A "dose" may also be a quantity of vaccine composition that is gradually administered to an animal using an extended release formulation and/or apparatus. In certain embodiments of the present invention, two or more doses of the vaccine composition are administered to an animal at different time points.

According to the present invention, an "immunologically-effective amount" of an influenza virus (e.g., an inactivated influenza virus) is an amount of influenza virus (usually expressed in terms of hemagglutinating units or "HA units") which will induce complete or partial immunity in a treated animal against subsequent challenge with a virulent strain of avian influenza virus. Complete or partial immunity can be assessed by observing, either qualitatively or quantitatively, the clinical symptoms of influenza virus infection in a vaccinated animal as compared to an unvaccinated animal after being challenged with virulent strains of avian influenza virus. Where the clinical symptoms of influenza virus infection in a vaccinated animal after challenge are reduced, lessened or eliminated as compared to the symptoms observed in an unvaccinated animal after a similar or identical challenge, the amount of influenza virus that was administered to the vaccinated animal is regarded as an "immunologically-effective amount".

A "cross-protective immune response" is one which protects against infection by a virus strain which is not identical to the one used to elicit the response.

As will be understood in the art, an "adjuvant" means one or more substances that enhance the immunogenicity and/or efficacy of a vaccine composition. Non-limiting examples of suitable adjuvants include squalane and squalene (or other oils of animal origin); block copolymers; detergents such as Tween-80; Quil A, mineral oils such as Drakeol or Marcol, vegetable oils such peanut oil; *Corynebacterium*-derived adjuvants such as *Corynebacterium parvum*; *Propionibacterium*-derived adjuvants such as *Propionibacterium acne*; *Mycobacterium bovis* (Bacille Calmette and Guerin or BCG); interleukins such as interleukin 2 and interleukin 12; monokines such as interleukin 1; tumor necrosis factor; interferons such as gamma interferon; surface active substances such as hexadecylamine, octadecylamine, octadecyl amino acid esters, lysolecithin, dimethyldioctadecylammonium bromide, N,N-dicoctadecyl-N', N'bis)2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; combinations such as saponin-aluminium hydroxide or Quil-A aluminium hydroxide; liposomes; mycobacterial cell wall extract; synthetic glycopeptides such as muramyl dipeptides or other derivatives; Avridine; Lipid A derivatives; dextran sulfate; DEAE-Dextran or with aluminium phosphate; carboxypolymethylene such as Carbopol'EMA; acrylic copolymer emulsions such as Neocryl A640; vaccinia or animal poxvirus proteins; sub-viral particle adjuvants such as cholera toxin, or mixtures thereof.

A therapeutic composition of the present invention can be formulated in an excipient that the object to be treated can tolerate. Examples of such excipients include water, saline, Ringer's solution, dextrose solution, Hank's solution, and other aqueous physiologically balanced salt solutions. Excipients can also contain minor amounts of additives, such as substances that enhance isotonicity and chemical or biological stability. Examples of buffers include phosphate buffer, bicarbonate buffer, and Tris buffer, while examples of stabilizers include A1/A2 stabilizer, available from Diamond Animal Health, Des Moines, Iowa.

Acceptable protocol to administer therapeutic compositions in an effective manner includes individual dose size, number of doses, frequency of dose administration, and mode of administration. Determination of such protocols can be accompanied by those skilled in the art, and examples are disclosed herein.

Administering or administer is defined as the introduction of a substance into the body of an individual and includes oral, nasal, ocular, rectal, vaginal and parenteral routes. Compositions may be administered individually or in combination with other agents via any route of administration, including but not limited to subcutaneous (SQ), intramuscular (IM), intravenous (IV), intraperitoneal (IP), intradermal (ID), via the nasal, ocular or oral mucosa (IN) or orally.

The dose administered to a patient, in the context of the present invention, should be sufficient to effect a beneficial response in a patient over an appropriate period of time. The quantity of agents to be administered may depend on the subject to be treated inclusive of the age, sex, weight and general health condition thereof, factors that will depend on the judgment of the practitioner.

Immunotherapeutic compositions of the invention may be used to prophylactically or therapeutically immunize animals such as humans. However, other animals are contemplated, preferably vertebrate animals including domestic animals such as livestock and companion animals.

The vaccine may be used in combination with others; for example, priming with an attenuated vaccine follows with a boost using the inactivated vaccine.

The invention encompasses all pharmaceutical compositions comprising an antigen, an adjuvant, and a pharmaceutically acceptable carrier.

Pharmaceutically acceptable carriers preferred for use in the present invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose", and the like. Preservatives and other additives may also be present such as, for example, antimicrobials, antioxidants, chelating agents, and inert gases and the like.

EXAMPLES

The following examples are provided for the sole purpose of illustrating the principles of the present invention; they are by no means intended as limitations of the present invention.

I. Recombinant HA Antigenic Protein

HA was from PR8, a well known H1N1 virus. The amino acid sequence of wild type H1HA is shown in SEQ ID NO 4 (565 amino acids); the recombinant H1HA is shown in SEQ ID NO 5, where two amino acids in the TMD were mutated into cysteines (S538C and L542C), designated as H12C. The mutations were achieved by the point mutation method.

Both H1WT and H12C were subcloned into a pFast-Bac vector (Invitrogen, Carlsbad, Calif., USA) first, and the baculovirus recombinants (rBacH1WT and rBacH12C) were prepared and used to infect *Spodoptera frugiperda* Sf9 cells to express the recombinant HA proteins. The expressed recombinant H1WT and H12C were purified and verified by Western blot; their functions were tested.

II. In Vivo Expression Vector Comprising the Recombinant HA Antigenic Protein

H1WT and H12C are cloned into in vivo expression vectors such as adenovirus vectors, vaccinia vectors, adeno-associated virus vectors, lentivirus vectors. They are used for DNA vaccine for immunization. Their efficiency for eliciting cross reactive immune responses is tested for their cross-reaction with inter-subtypic (e.g., H3N2, H5N1) or intra-subtypic viruses.

III. Virus-Like Particles Comprising the Recombinant HA Antigenic Protein

1. Cell Lines

*Spodoptera frugiperda* Sf9 cells were maintained in serum-free SF90011 medium (GIBCO, Grand Island, N.Y.) at 28° C. in spinner flasks at a speed of 100 rpm.

2. Generation of Recombinant Baculoviruses

A Bac-to-Bac baculovirus expression system is used for the generation of recombinant baculoviruses vectors expressing a recombinant HA protein (H1WT (SEQ ID NO 4), H12C (SEQ ID NO 5)). Other components are also amplified from PR8. Followed by PCR using specific primers annealing to the 3' and 5' terminus of each gene, fragments containing HA, NA, M1 and NP genes are cloned into the pFast-Bac-Dual vector (Invitrogen, Carlsbad, Calif., USA). Recombinant bacmids are generated by site-specific homologous recombination and transformation of the influenza genes-containing plasmid into *E. coli* DH10-Bac competent cells, which contained the AcMNPV baculovirus genome (Invitrogen). 1 µg of purified recombinant bacmid DNA is transfected into *Spodoptera frugiperda* Sf9 insect cells seeded in 6-well plates at $5 \times 10^5$ cells/ml using CellFectin reagent (Invitrogen). Cells are incubated for 3 days, and the virus harvested from the supernatant is subjected to three rounds of plaque purification.

3. Formation and Purification of Influenza VLPs

Influenza VLPs are attained by co-infection of Sf9 insect cells with baculovirus recombinants. Sf9 cells are seeded at a density of $2 \times 10^6$ per flask and allowed to settle at room temperature for 30 min. Subsequently, the Sf9 insect cells are co-infected with rBVs at multiplicities of infection (MOI) of 3-5 and incubated for 72 h at 28° C. Culture supernatant (200 ml) from Sf9 cells are harvested and clarified by centrifugation for 30 min at 2000×g at 4° C. The VLPs in the supernatant are pelleted by ultracentrifugation for 60 min at 100,000×g at 4° C. The sedimented particles resuspended in 1 ml of phosphate buffered saline (PBS) solution (pH 7.2) are loaded onto a 20%-30%-60% (w/v) discontinuous sucrose step density gradient and sedimented by ultracentrifugation for 60 min at 100,000×g at 4° C. The VLPs bands are collected and analyzed by SD S-PAGE and Western blot.

IV. Recombinant Influenza Virus Comprising the Recombinant HA Antigenic Protein

Reverse genetics was employed to produce the recombinant influenza virus. Two recombinant influenza viruses were rescued, one containing H1WT and one containing H12C; both shared the same genetic background (i.e., the remaining seven segments were derived from PR8). The H12C virus had higher resistance to pH and temperature treatments than the H1WT, indicating that the introduction of the 2C into the TM domain stabilized the HA homotrimer. The rescued recombinant influenza viruses were amplified in embryonated chicken eggs, and inactivated with 0.1% formalin. The inactivated viruses were mixed with complete Freud adjuvant to produce the vaccine (5 ug/dose) for the first immunization of Balb/c mice (5 per group); for the second immunization, incomplete Freud adjuvant was used. Two weeks after the second immunization, the sera were obtained from different groups and tested against one H3N2 strain virus using ELISA. The ELISA results (sera were diluted 1,600 times) are shown in the Table 2.

TABLE 2

| ELISA results of H1WT sera and H12C sera against purified H1WT, H12C and H3N2 | | | |
|---|---|---|---|
| Serum source | H1WT | H12C | H3N2 |
| H1WT | 0.784 | 0.708 | 0.166 |
| H12C | 0.426 | 0.563 | 0.219 |

From Table 2, the sera from the group immunized with H12C had a lower titer than that from the group immunized with H1WT when they are compared with titers against H1WT and H12C antigens. However, the titer against H3N2 from H12C is higher than that from H1WT, demonstrating that the introduction of a pair of two cysteines forming a CxxxC mini-domain (SEQ ID NO 2) into the TMD of H1 HA increased its capacity of eliciting stronger cross-reactive immune responses.

V. Recombinant HIV Env Antigenic protein expression vector pcDNA 3.1 and pFastBac Dual were from Invitrogen.

The DNA fragments encoding the extracellular domain of Env (SEQ ID NO 6) (gp140) and the TMD of H3 HA (SEQ ID NO 7) were separated amplified and ligated, where the protease site in the extracellular domain was eliminated by site-directed mutation. The ligated Env-H3TMD was cloned into pcDNA 3.1 for being used as DNA vaccine and pFastBac Dual for making VLP.

VI. Animal studies 6-8 weeks-old Balb/C mice (5 per group) were intramuscularly immunized with 30 ug three times (sera were collected one week after immunization), and followed by mucosal immunization (nose) three times with VLP (sera were collected two weeks after immunization). ELISA results showed that the group immunized with pcDNA-gp140TM had the highest titer against HIV VLP. It demonstrated that the introduction of the H3TMD with a two-cysteine mini-domain enhanced its antigenicity.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. A recombinant viral surface antigenic protein, wherein the viral surface antigenic protein in its native state forms a homotrimer on the surface of an enveloped virus, comprising an alpha-helix transmembrane domain, wherein three of the alpha-helix transmembrane domains of three molecules of the recombinant viral surface antigenic protein form a trimeric bundle, and wherein each of the alpha-helix transmembrane domains in the trimeric bundle contains at least one two-cysteine mini-domain selected from CxxC (SEQ ID NO 3), CxxxC (SE( )ID NO 4) and CxxxxC (SEQ ID NO 5), where x represents any amino acids as long as they do not break the helix structure; wherein when only one of the at least one two-cysteine minidomain (SEQ ID NO 4) is CFLLC that is present in transmembrane domain, native influenza A virus H3 HA is excluded.

2. The recombinant viral surface antigenic protein of claim 1, wherein the enveloped virus is one selected from tile group consisting of herpesviruses, poxviruses, hepadnaviruses, flavivirus, togavirus, coronavirus, hepatitis D, orthomyxovirus, rhabdovirus, bunyavirus, filovirus, retroviruses, and hepadnavirus.

3. The recombinant viral surface antigenic protein of claim 1, wherein the recombinant viral surface antigenic protein is encoded by a DNA sequence, and the DNA sequence is cloned into an in vivo expression vector to obtain a recombinant viral surface antigenic protein expression vector; so that the recombinant viral surface antigenic protein expression vector is used as a DNA vaccine against the enveloped virus from which the viral surface antigenic protein is derived.

4. The recombinant viral surface antigenic protein of claim 1, wherein the recombinant viral surface antigenic protein is present in a virus-like particle, virosome, or a recombinant enveloped vitas.

5. An immunogenic composition against an enveloped virus, comprising:
   a recombinant viral surface antigenic protein, wherein the viral surface antigenic protein in its native state forms a homotrimer on the surface of the enveloped virus;
   wherein the recombinant viral surface antigenic protein comprises an alpha-helix transmembrane domain, wherein three of the alpha-helix transmembrane domains of three molecules of the recombinant viral surface antigenic protein form a trimeric bundle, and wherein each of the alpha-helix transmembrane domains in the trimeric bundle contains at least one two-cysteine mini-domain selected from CxxC (SEQ ID NO 3), CxxxC (SEQ ID NO 4) and CxxxxC (SEQ ID NO 5), where x represents any amino acids as long as they do not break the helix structure; wherein when only one of the at least one two-cysteine minidomain (SEQ ID NO 4) is CFLLC that is present in transmembrane domain, native influenza A virus H3 HA is excluded; and a pharmaceutically acceptable ingredient.

6. The immunogenic composition of claim 5, wherein the enveloped virus is one selected from the group consisting of herpesviruses, poxviruses, hepadnaviruses, flavivirus, togavirus, coronavirus, hepatitis D, orthomyxovirus, rhabdovirus, bunyavirus, filovirus, retroviruses and hepadnavirus.

7. The immunogenic composition of claim 5, wherein the recombinant viral surface antigenic protein is encoded by a DNA sequence, and the DNA sequence is cloned into an in vivo expression vector to obtain a recombinant viral surface antigenic protein expression vector; so that the recombinant viral suffice antigenic protein expression vector is used as a DNA vaccine against the enveloped virus from which the viral surface antigenic protein is derived.

8. The immunogenic composition of claim 5, wherein the recombinant viral surface antigenic protein is present in a virus-like particle, virosome, or a recombinant enveloped virus.

* * * * *

SEQUENCE LISTING

<160> NUMBER OF SEQ ID NOS: 7

<210> SEQ ID NO 1
<211> LENGTH: 4
<212> TYPE: PRT
<213> ORGANISM: Artificial
<220> FEATURE:
<223> OTHER INFORMATION: two-cysteine minidomain 1
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1

```
Cys Xaa Xaa Cys
1

<210> SEQ ID NO 2
<211> LENGTH: 5
<212> TYPE: PRT
<213> ORGANISM: Artificial
<220> FEATURE:
<223> OTHER INFORMATION: two-cysteine minidomain 2
<220> FEATURE:
<221> NAME/KEY: misc_feature
<222> LOCATION: (2)..(4)
<223> OTHER INFORMATION: Xaa can be any naturally occurring amino acid

<400> SEQUENCE: 2

Cys Xaa Xaa Xaa Cys
1               5

<210> SEQ ID NO 3
<211> LENGTH: 6
<212> TYPE: PRT
<213> ORGANISM: Artificial
<220> FEATURE:
<223> OTHER INFORMATION: two-cysteine minidomain 3
<220> FEATURE:
<221> NAME/KEY: misc_feature
<222> LOCATION: (2)..(5)
<223> OTHER INFORMATION: Xaa can be any naturally occurring amino acid

<400> SEQUENCE: 3

Cys Xaa Xaa Xaa Xaa Cys
1               5

<210> SEQ ID NO 4
<211> LENGTH: 565
<212> TYPE: PRT
<213> ORGANISM: Influenza A virus

<400> SEQUENCE: 4

Met Lys Ala Asn Leu Leu Val Leu Leu Cys

```
Leu Lys Asn Ser Tyr Val Asn Lys Gly Lys Glu Val Leu Val Leu
                180                 185                 190

Trp Gly Ile His His Pro Asn Ser Lys Glu Gln Gln Asn Leu Tyr
            195                 200                 205

Gln Asn Glu Asn Ala Tyr Val Ser Val Val Thr Ser Asn Tyr Asn Arg
210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 5
<211> LENGTH: 565
<212> TYPE: PRT
```

<213> ORGANISM: Artificial
<220> FEATURE:
<223> OTHER INFORMATION: H12C, the H1HA sequence shown in SEQ ID NO 4 with two mutations (S538C and L542C)

<400> SEQUENCE: 5

```
Met Lys Ala Asn Leu Leu Val Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
            195                 200                 205

Gln Asn Glu Asn Ala Tyr Val Ser Val Val Thr Ser Asn Tyr Asn Arg
210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
            275                 280                 285

His Glu Cys Asn Thr Lys Cys Gln Thr Pro Leu Gly Ala Ile Asn Ser
290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
            355                 360                 365

His Gln Asn Gl

```
Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
            405                 410                 415

Glu Lys Arg Met Glu Asn Leu Asn Lys Lys Val Asp Asp Gly Phe Leu
        420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
            485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Cys Ser Leu Val Cys Leu Val
530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 6
<211> LENGTH: 856
<212> TYPE: PRT
<213> ORGANISM: Human immunodeficiency virus

<400> SEQUENCE: 6

Met Arg Val Met Gly Ile Glu Arg Asn Tyr Pro Cys Trp Trp Thr Trp
1               5                   10                  15

Gly Ile Met Ile Leu Gly Met Ile Ile Cys Asn Thr Ala Glu Asn
            20                  25                  30

Leu Trp Val Thr Val Tyr Tyr Gly Val Pro Ile Trp Lys Asp Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Ser Pro
65                  70                  75                  80

Gln Glu Leu Lys Met Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Gln Leu Thr Pro Leu Cys Val Thr Leu
        115                 120                 125

Asp Cys Ser Tyr Asn Ile Thr Asn Asn Ile Thr Asn Ser Ile Thr Asn
    130                 135                 140

Ser Ser Val Asn Met Arg Glu Glu Ile Lys Asn Cys Ser Phe Asn Met
145                 150                 155                 160

Thr Thr Glu Leu Arg Asp Lys Asn Arg Lys Val Tyr Ser Leu Phe Tyr
                165                 170                 175

Lys Leu Asp Val Val Gln Ile Asn Asn Gly Asn Asn Ser Ser Asn Leu
            180                 185                 190
```

```
Tyr Arg Leu Ile Asn Cys Asn Thr Ser Ala Leu Thr Gln Ala Cys Pro
        195                 200                 205

Lys Val Thr Phe Glu Pro Ile Pro Ile His Tyr Cys Ala Pro Ala Gly
        210                 215                 220

Tyr Ala Ile Leu Lys Cys Asn Asp Lys Glu Phe Asn Gly Thr Gly Leu
225                 230                 235                 240

Cys Lys Asn Val Ser Thr Val Gln Cys Thr His Gly Ile Arg Pro Val
                245                 250                 255

Val Ser Thr Gln Leu Leu Leu Asn Gly Ser Leu Ala Glu Gly Lys Val
        260                 265                 270

Met Ile Arg Ser Glu Asn Ile Thr Asn Asn Val Lys Asn Ile Ile Val
        275                 280                 285

Gln Leu Asn Glu Ser Val Thr Ile Asn Cys Thr Arg Pro Asn Asn Asn
        290                 295                 300

Thr Arg Arg Ser Val Arg Ile Gly Pro Gly Gln Thr Phe Tyr Ala Thr
305                 310                 315                 320

Gly Asp Ile Ile Gly Asp Ile Arg Gln Ala His Cys Asn Val Ser Gly
                325                 330                 335

Ser Gln Trp Asn Lys Thr Leu His Gln Val Val Glu Gln Leu Arg Lys
        340                 345                 350

Tyr Trp Asn Asn Asn Thr Ile Ile Phe Asn Ser Ser Ser Gly Gly Asp
        355                 360                 365

Leu Glu Ile Thr Thr His Ser Phe Asn Cys Gly Gly Glu Phe Phe Tyr
        370                 375                 380

Cys Asn Thr Ser Gly Leu Phe Asn Ser Thr Trp Val Asn Gly Thr Ala
385                 390                 395                 400

Ser Ile Glu Asn Gly Thr Ile Thr Leu Pro Cys Arg Ile Lys Gln Ile
                405                 410                 415

Ile Asn Met Trp Gln Arg Val Gly Gln Ala Ile Tyr Ala Pro Pro Ile
        420                 425                 430

Gln Gly Val Ile Arg Cys Val Ser Asn Ile Thr Gly Leu Ile Leu Thr
        435                 440                 445

Arg Asp Gly Gly Gly Asn Ser Asn Glu Asn Glu Thr Phe Arg Pro Gly
        450                 455                 460

Gly Gly Asp Met Arg Asp Asn Trp Arg Ser Glu Leu Tyr Lys Tyr Lys
465                 470                 475                 480

Val Val Lys Ile Glu Pro Leu Gly Val Ala Pro Thr Lys Ala Arg Arg
                485                 490                 495

Arg Val Val Glu Arg Glu Lys Arg Ala Val Thr Leu Gly Ala Val Phe
        500                 505                 510

Ile Gly Phe Leu Gly Thr Ala Gly Ser Thr Met Gly Ala Ala Ser Ile
        515                 520                 525

Thr Leu Thr Val Gln Ala Arg Lys Leu Leu Ser Gly Ile Val Gln Gln
530                 535                 540

Gln Ser Asn Leu Leu Arg Ala Ile Glu Ala Gln Gln His Leu Leu Lys
545                 550                 555                 560

Leu Thr Val Trp Gly Ile Lys Gln Leu Gln Ala Arg Val Leu Ala Val
                565                 570                 575

Glu Arg Tyr Leu Arg Asp Gln Gln Leu Leu Gly Ile Trp Gly Cys Ser
        580                 585                 590

Gly Lys Leu Ile Cys Pro Thr Asn Val Pro Trp Asn Ser Ser Trp Ser
        595                 600                 605
```

```
Asn Lys Ser Leu Asp Glu Ile Trp Asp Asn Met Thr Trp Leu Gln Trp
    610                 615                 620

Asp Lys Glu Ile Ser Asn Tyr Thr Ile Lys Ile Tyr Glu Leu Ile Glu
625                 630                 635                 640

Glu Ser Gln Ile Gln Gln Glu Arg Asn Glu Lys Asp Leu Leu Glu Leu
                645                 650                 655

Asp Lys Trp Ala Ser Leu Trp Asn Trp Phe Asp Ile Ser Lys Trp Leu
                660                 665                 670

Trp Tyr Ile Lys Ile Phe Ile Met Ile Val Gly Gly Leu Ile Gly Leu
                675                 680                 685

Arg Ile Val Phe Ala Val Leu Ser Val Ile Asn Arg Val Arg Gln Gly
    690                 695                 700

Tyr Ser Pro Leu Ser Phe Gln Thr His Thr Pro Asn Pro Arg Gly Leu
705                 710                 715                 720

Asp Arg Pro Gly Arg Ile Glu Glu Glu Gly Gly Glu Gln Asp Arg Gly
                725                 730                 735

Arg Ser Ile Arg Leu Val Ser Gly Phe Leu Ala Leu Ala Trp Asp Asp
                740                 745                 750

Leu Arg Asn Leu Cys Leu Phe Ser Tyr His Arg Leu Arg Asp Phe Ile
            755                 760                 765

Leu Ile Ala Ala Arg Thr Val Glu Leu Leu Gly His Ser Ser Leu Lys
    770                 775                 780

Gly Leu Arg Leu Gly Trp Glu Gly Leu Lys Tyr Leu Gly Asn Leu Leu
785                 790                 795                 800

Leu Tyr Trp Gly Arg Glu Leu Lys Ile Ser Ala Ile Asn Leu Leu Asp
                805                 810                 815

Thr Ile Ala Ile Ala Val Ala Gly Trp Thr Asp Arg Val Ile Glu Thr
                820                 825                 830

Val Gln Arg Leu Gly Arg Ala Ile Leu Asn Ile Pro Arg Arg Ile Arg
            835                 840                 845

Gln Gly Phe Glu Arg Ala Leu Leu
    850                 855

<210> SEQ ID NO 7
<211> LENGTH: 27
<212> TYPE: PRT
<213> ORGANISM: Artificial
<220> FEATURE:
<223> OTHER INFORMATION: H3HA transmembrane domain

<400> SEQUENCE: 7

Asp Trp Ile Leu Trp Ile Ser Phe Ala Ile Ser Cys Phe Leu Leu Cys
1               5                   10                  15

Val Val Leu Leu Gly Phe Ile Met Trp Ala Cys
            20                  25
```